US006896885B2

(12) United States Patent
Hanna

(10) Patent No.: US 6,896,885 B2
(45) Date of Patent: May 24, 2005

(54) COMBINED USE OF ANTI-CYTOKINE ANTIBODIES OR ANTAGONISTS AND ANTI-CD20 FOR TREATMENT OF B CELL LYMPHOMA

(75) Inventor: Nabil Hanna, Rancho Santa Fe, CA (US)

(73) Assignee: Biogen Idec Inc., San Diego, CA (US)

( * ) Notice: Subject to any disclaimer, the term of this patent is extended or adjusted under 35 U.S.C. 154(b) by 0 days.

(21) Appl. No.: 09/822,672

(22) Filed: Apr. 2, 2001

(65) Prior Publication Data

US 2002/0012665 A1 Jan. 31, 2002

Related U.S. Application Data

(60) Provisional application No. 60/193,467, filed on Mar. 31, 2000.

(51) Int. Cl.⁷ .............................................. A61K 39/395
(52) U.S. Cl. .............................. 424/156.1; 530/388.85; 530/388.23; 530/387.3; 424/1.11
(58) Field of Search .............................. 424/1.11, 130.1, 424/133.1, 141.1, 145.1, 156.1, 155.1, 158.1; 530/387.1, 387.3, 388.1, 388.22, 388.8, 388.85

(56) References Cited

U.S. PATENT DOCUMENTS

| | | |
|---|---|---|
| 5,231,012 A | 7/1993 | Mossman et al. |
| 5,286,850 A | 2/1994 | Gansow |
| 5,595,721 A | 1/1997 | Kaminski |
| 5,639,600 A | 6/1997 | McGrath |
| 5,677,180 A | 10/1997 | Robinson |
| 5,716,612 A | 2/1998 | Rybak |
| 5,736,137 A | 4/1998 | Anderson |
| 5,770,190 A | 6/1998 | Bruserud et al. |
| 5,789,554 A | 8/1998 | Leung et al. |
| 5,837,232 A | 11/1998 | DeWaal Malefyt et al. |
| 5,837,293 A | 11/1998 | De Waal Malefyt |
| 5,863,796 A | 1/1999 | Moore et al. |
| 5,871,725 A | 2/1999 | Schwarz |
| 6,090,365 A | 7/2000 | Kaminski |
| 6,106,823 A | 8/2000 | Vierira et al. |
| 6,113,898 A | 9/2000 | Anderson |
| 6,183,744 B1 * | 2/2001 | Goldenberg |
| 6,207,154 B1 | 3/2001 | Mossman et al. |
| 6,217,857 B1 | 4/2001 | Mossman et al. |
| 6,239,260 B1 | 5/2001 | Mossman et al. |
| 6,306,393 B1 | 10/2001 | Goldenberg |
| 6,319,493 B1 | 11/2001 | Vierira et al. |
| 6,423,500 B1 | 7/2002 | Moore et al. |
| 6,455,043 B1 | 9/2002 | Grillo-Lopez |
| 2002/0012665 A1 | 1/2002 | Hanna |

FOREIGN PATENT DOCUMENTS

| | | |
|---|---|---|
| DE | 295 12 719 U | 8/1996 |
| EP | 0567450 B1 | 6/1999 |
| WO | WO 94 04180 | 3/1994 |
| WO | WO 95/03411 A1 | 2/1995 |
| WO | WO98/56418 | 12/1998 |
| WO | WO00/20864 | 4/2000 |

OTHER PUBLICATIONS

Paul., Fundamental Immunology, chapter 8, Raven Press, NY, p. 242, 1993.*

Levy et al., J. Clin. Invest 93:424–428, 1994.*

Alas et al ., Blood vol. 92, No. 10 Suppl. 1 part 1–2, pp 601A, 1998.*

Czuczman et al., "Treatment of Patients with Low–Grade B–Cell Lymphoma . . . " Journal of Clinical Oncology, Jan. 1999, vol. 17, No. 1, Philadelphia, PA.

Demidem Aicha et al., "Chimeric Anti–CD20 (IDEC–C2B8) Monoclonal Antibody sensitizes a B–cell.." Cancer Biotherapy & Radiopharmaceuticals, 1997, pp. 177–186, vol. 12, No. 3.

Buske, C. et al., "Monoclonal Antibody Therapy for B–Cell Non–Hodgkin's Lymphmas: Emerging . . . " European Journal of Cancer, Pergamon Press, 1999, pp. 549–557, Oxford GB.

Cortes, J. et al., "Interleukin–10 in Non–Hodgkin's Lymphoma" Leukemia and Lymphoma, Harwood Academic Publishers, Jul. 1997, vol. 26, No. 3/4 pp. 251–259, Chur, CH.

Levy, Y. et al., "Interleuken–10 Prevent Spontaneious Death of Germinal Center B Cells by Induction of the B Cells by Induction of the bcl–2 Protein", J. Cin. Inves. vol. 93 (Jan. 1994) pp. 424–428.

Alas, S. et al., Chimeric Anti–CD20(C2B8)–Mediated Sensitization of B Cell Lymphoma to Cytotoxic Agents: Role of C2B8 . . . , Abstract#2479, Blood (No. 15, 1998) vol. 92, Supp. Pat1–2, pp. 601A.

Berzofsky, J. et al. , "Fundamental Immunology", Ch. 8, p. 242, (1993), Ed. William E. Paul.—Immunogencicity and Antigen Structure.

(Continued)

Primary Examiner—Larry R. Helms
(74) Attorney, Agent, or Firm—Pillsbury Winthrop LLP

(57) ABSTRACT

The present invention discloses combined therapies for treating hematologic malignancies, including B cell lymphomas and leukemias or solid non-hematologic tumors, comprising administration of anti-cytokine antibodies or antagonists to inhibit the activity of cytokines which play a role in perpetuating the activation of B cells. The administration of such antibodies and antagonists, particularly anti-IL10 antibodies and antagonists, is particularly useful for avoiding or decreasing the resistance of hematologic malignant cells or solid tumor cells to chemotherapeutic agents and anti-CD20 or anti-CD22 antibodies.

The invention also provides combination therapies for solid tumors having B cell involvement comprising the administration of an anti-cytokine antibody and a B cell depleting antibody such as RITUXAN® (rituximab).

29 Claims, No Drawings

OTHER PUBLICATIONS

Bonnefoix et al., "Growth Modulation of Freshly Isolated Non–Hodgkin's B– Lymphoma Cells Induced by Various Cytokines and All–Trans–Retinoic–Acid," *Leukemia and Lymphoma,* 25:169–178.

Beatty PR et al., "Involvement of IL–10 in the autonomous growth of EBV–transformed B cell lines," *J Immunol,* 1997, 158: 4045–4051.

Bonavida B et al., "Synergy is documented in vitro with low–dose recombinant tumor necrosis factor, cisplatin, and doxorubicin in ovarian cancer cells," *Gynecol Oncol,* 1990, 38: 333–339.

Cortes J et al., "Interleukin–10 in non–Hodgkin's lymphoma," *Leuk Lymphoma,* 1997, 26: 251–9.

Dedoussis GV et al., "Endogenous interleukin 6 conveys resistance to cis– diamminedichloroplatinum–mediated apoptosis of the K562 human leukemic cell line," *Exp Cell Res,* 1999, 249: 269–278.

Hekman A et al., "Initial experience with treatment of human B cell lymphoma with anti–CD19 monoclonal antibody," *Cancer Immunol Immunother,* 1991, 32: 364–372.

Kiesel S et al., "Removal of cells from a malignant B–cell line from bone marrow with immunomagnetic beads and with complement and immunoglobulin switch variant mediated cytolysis," *Leuk Res,* 1987, 11: 1119–1125.

Mosmann TR et al., "Isolation of monoclonal antibodies specific for IL–4, IL–5, IL–6, and a new Th2– specific cytokine (IL–10), cytokine synthesis inhibitory factor, by using a solid phase radioimmunoadsorbent assay," *J Immunol,* 1990, 145: 2938–2945.

Press OW et al., "Monoclonal antibody 1F5 (anti–CD20) serotherapy of human B cell lymphomas," *Blood,* 1987, 69: 584–591.

Stasi R et al., "Clinical implications of cytokine and soluble receptor measurements in patients with newly–diagnosed aggressive non–Hodgkin's lymphoma," *Eur J Haematol,* 1995, 54: 9–17.

Vlasveld LT et al., "Treatment of low–grade non–Hodgkin's lymphoma with continuous infusion of low–dose recombinant interleukin–2 in combination with the B–cell–specific monoclonal antibody CLB– CD19," *Cancer Immunol Immunother,* 1995, 40: 37–47.

Voorzanger N et al., "Interleukin (IL)–10 and IL–6 are produced in vivo by non–Hodgkin's lymphoma cells and act as cooperative growth factors," *Cancer Res,* 1996, 56: 5499–5505.

Wang Z et al., "Sensitization by interleukin–1alpha of carboplatinum anti–tumor activity against human ovarian (NIH:OVCAR–3) carcinoma cells in vitro and in vivo," *Int J Cancer,* 1996, 68: 583–587.

Yonish–Rouach E et al., "Wild–type p53 induces apoptosis of myeloid leukaemic cells that is inhibited by interleukin–6," *Nature,* 1991, 352: 345–347.

*Idec Pharmaceuticals and Corixa Corp.,* Case No. 01–1637–IEG [Doc. Nos. 486, 584] (S.D. Cal. Oct. 14, 2003).

*Biogen Idec v. Corixa Corp.,* Case No. 01–1637–IEG [Doc. Nos. 635, 662, 486] (S.D. Cal. Jan. 22, 2004).

Kaminski, et al., "Radioimmunotherapy of Advanced B–Cell Lymphoma with Non Bone Marrow Ablative Doses of 131–I MB–1 Antibody," 1990, *Antibody Immunoconjugates, and Radiopharmaceuticals,* vol. 3, No. 1, Abstract No. 83.

Kaminski, et al., "Radioimmunodetection (RID) and Non Marrow Ablative Radioimmunotherapy (RIT) of B–Cell Lymphoma With 131–I MB–1 Antibody," 1990, *Proceedings of ASCO,* vol. 9, p. 271, Abstract No. 1051.

Wahl, et al., "RadioImmunotherapy of B–Cell Lymphoma with I131 MB–1 Monoclonal Antibody," *The Journal of Nuclear Medicine: Proceedings of the 37th Annual Meeting,* p. 852, Abstract No. 622.

Kaminski, et al., "Phase I Trial Results of 131–I MB–1 Antibody Radioimmunotherapy (RAIT) of B–Cell Lymphoma," 1990, *Antibody Immunoconjugates, and Radiopharmaceuticals,* vol. 4, No. 1, p. 36, Abstract No. 66.

Kaminski, et al., "Phase I Evaluation of 131–I MB–1 Antibody Radioimmunotherapy (RIT) of B–Cell Lymphoma," 1990, *Blood,* vol. 76, No. 10, p. 355a, Abstract No. 1409.

Kaminski, et al., "Imaging, Dosimetry, and Radioimmunotherapy With Iodine 131–Labeled Anti–CD37 Antibody in B–Cell Lymphoma," 1992, *Journal of Clinical Oncology,* vol. 10, No. 11, pp. 1696–1711.

Jensen, et al., "Rapid tumor lysis in a patient with B–cell chronic lymphocytic leukemia and lymphocytosis treated with an anti–CD20 monoclonal antibody (IDEC C2B8, rituximab)," 1998, *Ann Hematol,* vol. 77, pp. 89–91.

\* cited by examiner

COMBINED USE OF ANTI-CYTOKINE ANTIBODIES OR ANTAGONISTS AND ANTI-CD20 FOR TREATMENT OF B CELL LYMPHOMA

CROSS REFERENCE TO RELATED APPLICATION

This application claims benefit of priority from U.S. Provisional Ser. No. 60/193,467, filed Mar. 31, 2000, and incorporated by reference herein.

FIELD OF THE INVENTION

The present invention concerns methods for treating hematologic malignancies including B cell lymphomas and leukemias with anti-cytokine agents such as antibodies and antagonists, where the targeted cytokines play a potentiating role in the disease process by stimulating hematologic malignant cells including B lymphoma and leukemia cells. Treatment with anti-cytokine agents in combination with other known therapies such as chemotherapy and administration of therapeutic antibodies has been found to provide a synergistic effect.

The invention also embraces the treatment of solid non-hematologic (non-lymphoid) tumors, e.g., colorectal or liver cancer, which tumors are characterized by B cell involvement, by the administration of a cytokine antibody or cytokine antagonist, in combination with treatment with an antibody to a B cell target, e.g. CD20.

BACKGROUND OF THE INVENTION

The immune system of vertebrates (for example, primates, which include humans, apes, monkeys, etc.) consists of a number of organs and cell types which have evolved to: accurately and specifically recognize foreign microorganisms ("antigen") which invade the vertebrate-host; specifically bind to such foreign microorganisms; and, eliminate/destroy such foreign microorganisms. Lymphocytes, as well as other types of cells, are critical to the immune system and to the elimination and destruction of foreign microorganisms. Lymphocytes are produced in the thymus, spleen and bone marrow (adult) and represent about 30% of the total white blood cells present in the circulatory system of humans (adult). There are two major subpopulations of lymphocytes: T cells and B cells. T cells are responsible for cell mediated immunity, while B cells are responsible for antibody production (humoral immunity). However, T cells and B cells can be considered interdependent—in a typical immune response, T cells are activated when the T cell receptor binds to fragments of an antigen that are bound to major histocompatability complex ("MHC") glycoproteins on the surface of an antigen presenting cell; such activation causes release of biological mediators ("interleukins" or "cytokines") which, in essence, stimulate B cells to differentiate and produce antibody ("immunoglobulins") against the antigen.

Each B cell within the host expresses a different antibody on its surface—thus one B cell will express antibody specific for one antigen, while another B cell will express antibody specific for a different antigen. Accordingly, B cells are quite diverse, and this diversity is critical to the immune system. In humans, each B cell can produce an enormous number of antibody molecules (i.e., about $10^7$ to $10^8$). Such antibody production most typically ceases (or substantially decreases) when the foreign antigen has been neutralized. Occasionally, however, proliferation of a particular B cell will continue unabated; such proliferation can result in a cancer referred to as "B cell lymphoma."

Non-Hodgkin's lymphoma is one type of lymphoma that is characterized by the malignant growth of B lymphocytes. According to the American Cancer Society, an estimated 54,000 new cases will be diagnosed, 65% of which will be classified as intermediate- or high-grade lymphoma. Patients diagnosed with intermediate-grade lymphoma have an average survival rate of two to five years, and patients diagnosed with high-grade lymphoma survive an average of six months to two years after diagnosis.

Conventional therapies have included chemotherapy and radiation, possibly accompanied by either autologous or allogeneic bone marrow or stem cell transplantation if a suitable donor is available, and if the bone marrow contains too many tumor cells upon harvesting. While patients often respond to conventional therapies, they usually relapse within several months.

A relatively new approach to treating non-Hodgkin's lymphoma has been to treat patients with a monoclonal antibody directed to a protein on the surface of cancerous B cells. The antibody may be conjugated to a toxin or radiolabel thereby affecting cell death after binding. Alternatively, an antibody may be engineered with human constant regions such that human antibody effector mechanisms are generated upon antibody binding which result in apoptosis or death of the cell.

Rituximab® (IDEC Pharmaceuticals Corporation) is one of a new generation of monoclonal antibodies developed for the treatment of B cell lymphomas, and in particular, non-Hodgkin's lymphoma. Rituximab® is a genetically engineered anti-CD20 monoclonal antibody with murine light- and heavy-chain variable regions and human gamma I heavy-chain and kappa light-chain constant regions. Rituximab® is more effective than its murine parent in fixing complement and mediating ADCC, and it mediates CDC in the presence of human complement. The antibody inhibits cell growth in the B-cell lines FL-18, Ramos, and Raji, sensitizes chemoresistant human lymphoma cell lines to diphtheria toxin, ricin, CDDP, doxorubicin, and etoposide, and induces apoptosis in the DHL-4 human B-cell lymphoma line in a dose-dependent manner.

However, many patients are refractory to or relapse following Rituximab® therapy, as well as chemotherapy. Therefor, there still remains a need for lymphoma treatments which may be combined with Rituximab® therapy or chemotherapy in order to increase the chance of remission and decrease the rate of relapse in lymphoma patients.

Many groups have suggested using cytokines for the treatment of various types of cancers. For instance, Wang et al. suggested that cytokines are "directly cytotoxic to tumor cells" and showed that interleukin-1 alpha (IL1α) potentiated the anti-tumor effect of anti-tumor drugs against several human tumor cells in vitro (*Int. J. Cancer* (Nov. 27, 1996) 68(5): 583–587). Bonvida et al. disclose that cytokines have the potential to "enhance the efficacy of chemotherapeutic agents" and show that recombinant tumor necrosis factor and the chemotherapeutic agent cisplatin show a synergistic effect against ovarian cancer cells (*Gynecol. Oncol.* (September 1990) 38(3): 333–339). U.S. Pat. No. 5,716,612 teaches that IL-4 may be used to potentiate the effect of chemotherapeutic agents in the treatment of cancer.

However, some groups have also recognized that cytokines may play a detrimental role in the development of some cancers. For instance, interleukin-6 (IL6) has been known for the ability in some instances to inhibit apoptosis of leukemic cells. (See Yonish-Rouach et al. Wild type p53 induces apoptosis of myeloid leukemic cells and is inhibited by interleukin-6. *Nature* 352: 345–347 (1991)). Recently it was shown that IL6 may play a role in the resistance of some leukemic cells to anti-cancer chemotherapeutic agents, and that, in vitro, anti-IL6 antibody increases the sensitivity of cisplatin-resistance K562 cells to cisplatin-induced apoptosis. (See Dedoussis et al. Endogenous interleukin 6 conveys resistance to cis-diamminedichloroplatinum-mediated apoptosis of the K562 human leukemic cell line).

A potentiating effect on B cells has also been postulated for IL10, the production of which has been reported to be upregulated in some cell lines derived from B cell lymphomas (See Cortes et al. Interleukin-10 in non-Hodgkin's lymphoma. *Leuk Lymphoma* 26(3–4): 251–259 (July, 1997). However, when the serum of NHL patients was tested for correlation between IL10 levels and prognosis, more significance was placed on the levels of viral IL10, which is produced from a homologous open reading frame BCFR1, located in the genome of the Epstein Barr Virus (EBV). In fact, another group reported at about the same time that IL10 was an autocrine growth factor for EBV-infected lymphoma cells. (See Beatty et al. Involvement of IL10 in the autonomous growth of EBV-transformed B cell lines. *J. Immunol.* 158(9): 4045–51 (May 1, 1997)). Alternatively, others have hypothesized that IL6 and IL10 production by macrophages plays a key role in the occurrence of lymphocytic diseases. (See U.S. Pat. No. 5,639,600).

It has also been reported that IL10 may work in combination with IL6, IL2 and TNF-alpha to increase proliferation of non-Hodgkin's lymphoma cells. (See Voorzanger et al. Interleukin-(IL)10 and IL6 are produced in vivo by non-Hodgkin's lymphoma cells and act as cooperative growth factors. *Cancer Res.* 56(23): 5499–505 (Dec. 1, 1996). Also statistically significantly higher levels of IL2, IL6, IL8, IL10, soluble IL2 receptor, soluble transferrin receptor and neopterin were observed in NHL patients as compared to a control group, although no single parameter was found to be of prognostic significance. (See Stasi et al. Clinical implications of cytokine and soluble receptor measurements in patients with newly diagnosed non-Hodgkin's lymphoma. *Eur. J. Haemotol.* 54(1): 9–17 (January, 1995).

However, there have been just as many reports in the literature which have suggested that cytokines such as IL10 show no correlation to disease progression, and that such cytokines may actually be helpful in combating lymphoma rather than contributing to the disease. For instance, when Bonnefoix et al. tested the potential of ten cytokines (IL2, IL3, IL4, IL6, IL10, IL13, G-CSF, GM-CSF, interferon alpha and interferon gamma) to modulate the spontaneous proliferative response of B-non-Hodgkin's lymphoma cells of various histological subtypes, this group found that each cytokine could be either inhibitory or stimulatory depending on the sample, and that there was no relationship with different histological subtypes. In fact, U.S. Pat. No. 5,770,190, herein incorporated by reference, suggests administration of IL10 in conjunction with chemotherapeutic agents as a treatment for acute leukemia.

It would be a benefit to lymphoma patients if therapeutic regimens incorporating anti-cytokine antibodies could be devised whereby such antibodies could be used to increase the sensitivity of B lymphoma cells to other types of therapeutic drugs. It would be particularly helpful if anti-cytokine antibodies could be administered for the purpose of avoiding or overcoming the resistance of B lymphoma cells in lymphoma patients to chemotherapeutic agents, and for the purpose of potentiating the apoptotic activity of therapeutic antibodies. Such combined treatment regimens would add to the therapies available to lymphoma patients and potentially decrease the rate of relapse in these patients.

OBJECTS OF THE INVENTION

It is an object of the invention to provide a method of avoiding, decreasing or overcoming the resistance of hematologic malignant cells or solid non-hematologic tumor cells to at least one chemotherapeutic agent, comprising administering an anti-cytokine antibody or cytokine antagonist to a patient diagnosed with a hematologic malignancy prior, concurrent or after administration of at least one chemotherapeutic agent.

It is a more specific object of the invention to provide a method of avoiding, decreasing or overcoming the resistance of hematologic malignant cells to apoptosis induced by a therapeutic agent, comprising administering an anti-cytokine antibody or cytokine antagonist to a patient diagnosed with a hematologic malignancy.

It is another object of the invention to provide a method of treating a patient with a hematologic malignancy who has relapsed following chemotherapy, comprising administering an anti-cytokine antibody or cytokine antagonist to said patient.

It is another object of the invention to provide a method of treating a patient having a hematologic malignancy who is refractory to chemotherapy, comprising administering an anti-cytokine antibody or cytokine antagonist to said patient.

It is yet another object of the invention to provide a method of treating a patient with a hematologic malignancy who has relapsed following therapy with a therapeutic antibody, comprising administering an anti-cytokine antibody or cytokine antagonist to said patient.

It is still another object of the invention to provide a method of treating a patient with a hematologic malignancy who is refractory to therapy with a therapeutic antibody, comprising administering an anti-cytokine antibody or cytokine antagonist to said patient.

It is another object of the invention to provide a method of treating a B cell lymphoma patient comprising administering to said patient a therapeutically effective amount of an anti-CD20 antibody simultaneously with or consecutively with in either order an anti-cytokine antibody.

It is another object of the invention to provide a method of treating a solid non-hematologic (non-lymphoid) tumor wherein B cells elicit a pro-tumor response by the administration of an anti-cytokine antibody, e.g. an anti-IL10 antibody and at least one B cell depleting antibody, e.g. an anti-CD20 antibody.

It is a more specific object of the invention to provide a method of treating solid, non-lymphoid tumor involving the digestive system, especially colorectal cancer or liver cancer by the administration of an anti-cytokine antibody, preferably an anti-IL10 antibody and a B cell depleting antibody, particularly a depleting anti-CD20 antibody.

SUMMARY OF THE INVENTION

In a first aspect, the present invention relates to the administration of anti-cytokine antibodies and cytokine antagonists, particularly antibodies to IL10, in combination with chemotherapy drugs and/or therapeutic antibodies to increase the response rate and response duration in patients with hematological malignancies such as B cell lymphomas and leukemias or solid non-hematologic tumors, such as breast cancer, ovarian cancer, testicular cancer and others.

Thus, the present invention relates to methods of treating hematologic malignancies such as B cell lymphomas and leukemias by administering to a patient having a hematologic malignancy such as B cell lymphoma or a leukemia, antibodies directed to B cell receptors and antibodies or antagonists which interfere with the action of certain cytokines. In particular, the present invention relates to administration of antibodies to B cell markers which initiate apoptosis of B lymphoma cells, such as anti-CD20, anti-CD22, anti-CD40, anti-CD23, anti-CD19, anti-CD37 and others identified infra, and antibodies to or antagonists of cytokines which may interfere with apoptosis, e.g., anti-IL10. Combined therapeutic regimens including other treatments which would also benefit from anti-cytokine therapy, i.e., chemotherapy, are also encompassed. The methods will find use in particular for treating patients having hematological malignancies such as B lymphomas or leukemias characterized by cells that have become resistant to chemotherapeutic agents and therapeutic antibodies.

In a second aspect, the present invention provides novel methods of treating solid non-hematologic (non-lymphoid) tumors having B cell involvement (but not of B cell origin), particularly cancers wherein B cells elicit a pro-tumor response by the administration of an antibody to a cytokine, e.g., IL10, in conjunction with B cell specific antibody therapy, particularly a B cell depleting antibody, and preferably CD20 antibody therapy, optionally in combination with radiotherapy or chemotherapy. Examples of such solid tumors include colorectal cancer, liver cancer, breast cancer, lung cancer, prostate cancer, stomach cancer, head and neck cancer, ovarian cancer, testicular cancer, esophageal cancer and others. Suitable chemotherapies are discussed infra. These cancers may comprise precancers, Stage I and II cancers, and advanced cancers, e.g. past Stage II and including solid tumors that have metastasized.

DETAILED DESCRIPTION OF THE INVENTION

In a first aspect, the present invention includes methods of avoiding, decreasing or overcoming the resistance of hematologic malignant cells including, e.g., B lymphoma and leukemia cells to at least one chemotherapeutic agent, comprising administering an anti-cytokine antibody or cytokine antagonist to a patient diagnosed with B cell lymphoma.

Often, such resistance by a hematologic malignancy patient's B cells is mediated by stimulation of the tumorigenic B cells by one or more cytokines such that the cells fail to respond to apoptotic signals. In such cases, the methods of the present invention may be described as methods of avoiding, decreasing or overcoming the resistance of such tumorigenic B cells to apoptosis, with chemotherapeutic agents being examples of agents which may induce apoptosis. Also encompassed are therapeutic antibodies directed to targets on the surface of B cells, such as anti-CD19, anti-CD20, anti-CD22, anti-CD40, and anti-CD28 and other B cell targets identified infra.

Because resistance of B cells is often only apparent after a patient has relapsed following, or is refractory to, a first treatment with a therapeutic agent, the methods of the present invention will often encompass treating patients with hematologic malignancies such as B cell lymphoma or leukemia who have relapsed following, or are refractory to, chemotherapy or therapy with a therapeutic antibody. However, the anti-cytokine antibodies and antagonists of the present invention may also be used in conjunction with other therapies or prior to other therapies in patients newly diagnosed with lymphoma to decrease the chance of relapse, and increase the length and duration of the response to therapy.

The methods of the present invention are appropriate to treat a wide variety of hematologic malignancies, especially B cell lymphomas and leukemias, including but not limited to low grade/follicular non-Hodgkin's lymphoma (NHL), small lymphocytic (SL) NHL, intermediate grade/ follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia, chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia. It should be clear to those of skill in the art that these lymphomas will often have different names due to changing systems of classification, and that patients having lymphomas and leukemias classified under different names may also benefit from the combined therapeutic regimens of the present invention.

For instance, a recent classification system proposed by European and American pathologists is called the Revised European American Lymphoma (REAL) Classification. This classification system recognizes Mantle cell lymphoma and Marginal cell lymphoma among other peripheral B-cell neoplasms, and separates some classifications into grades based on cytology, i.e., small cell, mixed small and large, large cell. It will be understood that all such classified lymphomas may benefit from the combined therapies of the present invention.

The U.S. National Cancer Institute (NCI) has in turn divided some of the REAL classes into more clinically useful "indolent" or "aggressive" lymphoma designations. Indolent lymphomas include follicular cell lymphomas, separated into cytology "grades," diffuse small lymphocytic lymphoma/chronic lymphocytic leukemia (CLL), lymphoplasmacytoid/Waldenstrom's Macroglobulinemia, Marginal zone lymphoma and Hairy cell leukemia. Aggressive lymphomas include diffuse mixed and large cell lymphoma, Burkitt's lymphoma/diffuse small non-cleaved cell lymphoma, Lymphoblastic lymphoma, Mantle cell lymphoma and AIDS-related lymphoma. All that is required is that the extent or duration of response to therapy be extended as a result of administration of said anti-cytokine antibody or antagonist. But the methods are most preferably used to treat patients having non-Hodgkin's lymphoma (NHL), where the present inventors have surprisingly found that administration of anti-cytokine antibodies and antagonists has a synergistic effect. Since the effect of cytokines and the identity of detrimental cytokines may vary among different patients and different types of lymphomas, and the effect of various cytokines on the resistance of B lymphoma cells may vary with different chemotherapeutic and immunotherapeutic agents, it is suggested that the levels of the respective cytokines in individual patients be tested before the patients are administered the anti-cytokine therapy.

In a second aspect, the invention provides a method of treating solid, non-hematologic tumors wherein B cells elicit a protein response (promote tumor growth and/or metastasis) comprising the administration of a anti-cytokine antibody, e.g. an anti-IL10 antibody, and an antibody to a B cell target, preferably an anti-CD20 antibody having B cell depleting activity. However, the invention includes the usage of antibodies to other B cell targets identified infra. Also, this aspect further includes the additional use of chemotherapy and/or radiotherapy.

A variety of chemotherapeutic agents have been applied to the treatment of different types of cancers, and the methods of the present invention will avoid, decrease or overcome the resistance of malignant, e.g. lymphoma, cells to at least one, but possibly several, of these chemotherapeutic agents. In particular, chemotherapies which may benefit by supplemental anti-cytokine therapy include but are not limited to CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP, DHAP, methotrexate, doxorubicin, daunorubicin, tamoxifen, toremifene, and cis-platin. Other chemotherapeutic agents are identified infra in the section relating to preferred embodiments.

There are likely to be a variety of cytokines which play a detrimental, stimulatory role in hematologic or non-hematologic malignancies including leukemic and lymphoma diseases, either alone or in cooperation with other cytokines. Thus, depending on the patient and the disease, more than one anti-cytokine antibody or antagonist may benefit a particular patient as a supplemental therapy. Those cytokines include but are not limited to IL2, IL6, IL10 and TNF-alpha. Other appropriate cytokines are identified infra in the preferred embodiments. For non-Hodgkin's lymphoma, the preferred anti-cytokine treatment will comprise anti-IL10 therapy.

There are several anti-IL10 antibodies which are known in the art and may be used for the purposes of the present invention. U.S. Pat. No. 5,871,725 describes a rat anti-human antibody designated 19F1. Another anti-IL10 antibody, alpha-IL10, is described in U.S. Pat. No. 5,837,293. Anti-IL10 antibodies are also described in Tim R. Mosmann, et al., "Isolation of Monoclonal Antibodies Specific For IL-4, IL-5, IL-6, and a New Th2-Specific Cytokine (IL-10), Cytokine Synthesis Inhibitory Factor, By Using A Solid Phase Radioimmunoadsorbent Assay," *The Journal of Immunology*, 145(9):2938–2945, Nov. 1, 1990. Antagonists may take the form of proteins which compete for receptor binding, e.g., which lack the ability to activate the receptor while blocking IL-10 binding, or IL-10 binding molecules, such as antibodies. The term antibody should be understood as encompassing antibody fragments as well as whole antibodies, i.e., Fab, Fab$_2$ and Fv fragments. Antibodies may be isolated by immunizing another animal with human IL-10, but then may be humanized using method known in the art to decrease their immunogenicity once they are administered to a human patient.

The appropriate dosage of anti-cytokine antibody will depend on the cytokine targeted, the results of preliminary serum profiles in individual patients, the type of lymphoma being treated and the stage of disease. For anti-IL10 antibodies in the treatment of newly diagnosed low-grade non-Hodgkin's lymphoma, the preferred dosage may range from 0.001 mg to 100 mg/kg, preferably from about 0.1 to 100 mg/kg, and most typically about 0.4 to 20 mg/kg body weight, depending on whether the antibody is administered concurrently with or prior to another therapeutic agent. Preferably, the anti-cytokine antibody is administered concurrent or prior to a chemotherapeutic agent or other therapy, typically from about one hour prior, to about one month prior, preferably within one to seven days prior to administration of chemotherapeutic or other agent.

Also included in the present invention are kits for accomplishing the disclosed methods. A kit according to the present invention comprises at least one anti-cytokine antibody or antagonist which may be readily admixed or resuspended with a pharmaceutically acceptable carrier and conveniently injected into a lymphoma patient. In cases where the serum of a lymphoma patient is preferably tested for cytokine profiles prior to administration of said anti-cytokine antibody or antagonist, the kit may also or alternatively comprise reagents and materials for testing the relative amounts of various cytokines in the patient's serum.

Also encompassed in the present invention are combined therapeutic methods of treating hematologic malignancies such as B cell lymphoma and leukemias comprising administering to a patient with a hematologic malignancy a therapeutically effective amount of a therapeutic antibody simultaneously with or consecutively with in either order an anti-cytokine antibody. Therapeutic antibodies are defined as those which bind to receptors on the surface of hematologic malignant cells, e.g., tumorigenic B cells, and mediate their destruction or depletion when they bind, i.e., anti-CD20, anti-CD19, anti-CD22, anti-CD21, anti-CD23, anti-CD37, and other B cell targets identified infra. While the anti-cytokine agents of the present invention will have some beneficial effect alone in that they block cytokine-mediated proliferation of tumorigenic B cells, the combined administration of the therapeutic antibodies with the anti-cytokine agents will have a synergistic effect in that the duration and/or extent of response will be better than the additive effect of both types of therapies applied independently.

While not wishing to be held to the following theory, the present inventors believe that the synergistic effects seen by co-administering the anti-cytokine agents of the present invention are related to the inhibition of the targeted cytokine which may usually have the effect to inhibit apoptosis. Accordingly, when the anti-cytokine agents of the present invention are combined with an agent which acts by inducing apoptosis, e.g., anti-CD20, anti-CD22, anti-CD19, anti-CD21, anti-CD23, or anti-CD40 antibodies, the combined administration shows a synergetic effect well beyond the additive effect of either agent alone.

Never-the-less, this does not preclude the use of the anti-cytokine antibodies and antagonists of the present invention in combined therapies with other antibodies or therapeutic agents whose efficacy is not facilitated via apoptosis. For instance, radiolabeled antibodies facilitate the destruction of tumor cells by binding to the B cell surface and delivering a lethal dose of radiation. Such antibodies, as well as antibodies conjugated to toxins, may also be used in conjunction with the anti-cytokine agents of the present invention. Preferred radiolabeled antibodies are those labeled with yttrium-[90] ($^{90}$Y). A particularly preferred radiolabeled antibody is Zevelin (IDEC Pharmaceuticals Corporation), which is an anti-CD20 antibody conjugated to $^{90}$Y.

The combined therapeutic methods of the present invention may further comprise administration of at least one chemotherapeutic agent or regimen, where such chemotherapy includes, by way of example, CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP, DHAP, doxorubicin, cisplatin, daunorubicin, tamoxifen, toremifene, and methotrexate as well as the additional chemotherapeutic agents identified infra. A preferred chemotherapeutic regimen for the treatment of non-Hodgkin's lymphoma patients is CHOP. The anti-cytokine antibody or antagonist is preferably administered prior to the B cell target antibody, e.g., anti-CD20, CD22, CD19 or CD40, and/or chemotherapy, such that proliferation of B lymphoma cells as a result of the targeted cytokine is quelled prior to administration of the B cell therapeutic. As described above, the target cytokine may be IL2, IL6, IL10 or TNF-alpha among others, depending on the patient's cytokine profile prior to treatment, but preferably the targeted cytokine is IL10.

As mentioned above, therapeutic antibodies of the present invention may be any antibody which targets a molecule expressed on the surface of B cells, particularly one having B cell depleting activity. A listing of suitable B cell targets is identified infra.

Depending on the patient and extent of disease, the anti-B cell target binding antibody, e.g., Rituximab® may be administered at a dosage ranging from 0.01 to about 100 mg/kg, more preferably from about 0.1 to 50 mg/kg, and most preferably from about 0.4 to 20 mg/kg of body weight. Effective dosages may be lower in combined therapeutic regimens which include anti-cytokine agents, because the proliferative potential of B lymphoma cells will be reduced. Again, effective doses will depend on the chosen anti-cytokine therapy, and the relative levels of potentiating cytokine in the patient's serum.

The combined therapies of the present invention are also suitable for treating a wide range of lymphomas, including but not limited to low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia, chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia. Preferred targeted diseases are non-Hodgkin's lymphoma (NHL), and particularly low-grade, follicular NHL. Again, it may be helpful for the serum of the lymphoma patient to be tested for cytokine profiles prior to administration of the anti-cytokine antibody or antagonist.

As already discussed, the combination therapies provided herein, particularly the combined usage of an anti-cytokine antibody, e.g. anti-IL10 and an anti-B cell target antibody, e.g. anti-CD20, are also useful for treating solid, non-hematologic (non-lymphoid) cancers, including by way of example, colorectal cancer, liver cancer, and other digestive cancers, breast cancer, esophageal cancer, head and neck cancer, lung cancer, ovarian cancer, prostate cancer and testicular cancer. These cancers my be in early, intermediate or advanced stages, e.g. metastasis.

The present invention also encompasses kits for administering the therapeutic antibody and the anti-cytokine antibody or antagonist according to the disclosed methods. Kits may comprise more than one type of therapeutic antibody and more than one anti-cytokine agent. Kits may also comprise reagents and materials for testing cytokine profile prior to administration of the therapeutic antibody and anti-cytokine antibody or antagonist.

As noted, the invention further embraces the treatment of solid, non-lymphoid tumors by the administration of an anti-cytokine antibody, e.g., an anti-IL10 antibody, and a B cell specific antibody, preferably an antibody having substantial B cell depleting activity such as RITUXAN® (rituximab). It has been reported that some solid tumors apparently have B cell involvement. That is to say that the B cells are somehow involved in promoting or maintaining the tumorigenic state and may impede the body's immune defense system against such tumor. With respect thereto, WO 020864 A1, incorporated by reference herein, which identifies Biocrystal Inc. as the Applicant describes the treatment of solid, non-lymphoid tumor using antibodies that target B cells including RITUXAN® (rituximab). It was reported therein that this treatment resulted in pronounced anti-tumor responses, even in patients with advanced colorectal cancer, lung cancer and liver cancer.

By contrast, the present invention provides an improved combination therapy, wherein solid, non-lymphoid tumors are treated by use of an anti-cytokine antibody, such as anti-IL10 and a B cell depleting antibody, such as an anti-CD20 antibody.

This combination regimen should afford an enhanced method of treating solid tumors, particularly those wherein B cells are involved, but are not themselves the cancerous cells. In this regimen, the cytokine antagonist, e.g., anti-cytokine antibody and the B cell depleting antibody, e.g., RITUXAN® (rituximab) will be administered separately or together and in either order.

Additionally, this regimen may include the use of radiotherapy, e.g., external beam irradiation, total body irradiation, radioimmunotherapy or chemotherapy. Suitable chemotherapies are identified infra. The radioimmunotherapy may comprise treatment with a radiolabeled antibody that binds a target expressed by the solid tumor.

Typically, the anti-cytokine antibody will be administered prior to the B cell depleting antibody. It is anticipated that this combination therapy will be suitable for treating any solid tumor having B cell involvement. Suitable examples of solid tumors have been identified previously. One noteworthy example is colorectal cancer.

In this embodiment, the B cell depleting antibody and cytokine will be administered such that it s delivered to the solid tumor site. Preferably, the antibodies will be injected proximate or directly at the tumor site, e.g., by intravenous injection at a vein proximate to the tumor.

This combination regimen cell results in remission or shrinkage of the solid tumor, e.g., a lung or colorectal tumor.

DETAILED DESCRIPTION OF THE PREFERRED EMBODIMENTS

In order to further describe the preferred embodiments and full scope of the invention, the following definitions are provided.

I. Definitions

"Cytokine antagonist" is a compound that inhibits or blocks the expression and/or activity of a cytokine, e.g. an interleukin or interferon or another cytokine.

A "B cell surface marker" or "B cell target" or "B cell antigen" herein is an antigen expressed on the surface of a B cell which can be targeted with an antagonist which binds thereto. Exemplary B cell surface markers include the CD10, CD19, CD20, CD21, CD22, CD23, CD24, CD37, CD53, CD72, CD73, CD74, CDw75, CDw76, CD77, CDw78, CD79a, CD79b, CD80, CD81, CD82, CD83, CDw84, CD85 and CD86 leukocyte surface markers: The B cell surface marker of particular interest is preferentially expressed on B cells compared to other non-B cell tissues of a mammal and may be expressed on both precursor B cells and mature B cells. In one embodiment, the marker is one, like CD20 or CD19, which is found on B cells throughout differentiation of the lineage from the stem cell stage up to a point just prior to terminal differentiation into plasma cells. The preferred B cell surface markers herein are CD19 and CD20.

The "CD20" antigen is a ~35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35". The CD20 antigen is described in Clark et al. PNAS (USA) 82:1766 (1985), for example. The "CD19" antigen refers to a ~90 kDa antigen identified, for example, by the HD237-CD19 or 134 antibody (Kiesel et al. *Leukemia Research* 11, 12:1119 (1987)). Like CD20, CD19 is found on cells throughout differentiation of the lineage from the stem cell stage up to a point just prior to terminal differentiation into plasma cells. Binding of an antagonist to CD19 may cause internalization of the CD19 antigen.

A "hematologic malignancy" includes any malignancy associated with cells in the bloodstream. Examples thereof include B and T cell lymphomas, leukemias including but not limited to low grade/follicular non-Hodgkin's lymphoma (NHL), small lymphocytic (SL) NHL, intermediate grade/ follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia, chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, and promyelocytic leukemia. It should be clear to those of skill in the art that these lymphomas will often have different names due to changing systems of classification (as previously discussed), and that patients having lymphomas and leukemias classified under different names may also benefit from the combined therapeutic regimens of the present invention.

A solid, non-hematologic (non-lymphoid) tumor refers to a non-hematologic malignancy having B cell involvement, i.e., where B cells are involved in a "protumor" response. Such solid tumors are characterized by palpable tumors, typically at least 0.5 mm in diameter, more typically at least 1.0 mm in diameter. Examples thereof include colorectal cancer, liver cancer, breast cancer, lung cancer, head and neck cancer, stomach cancer, testicular cancer, prostate cancer, ovarian cancer, uterine cancer and others. These cancers may be in the early stages (precancer), intermediate (Stages I and II) or advanced, including solid tumors that have metastasized. These solid tumors will preferably be cancers wherein B cells elicit a protumor response, i.e. the presence of B cells is involved in tumor development, maintenance or metastasis.

A B cell "antagonist" is a molecule which, upon binding to a B cell surface marker, destroys or depletes B cells in a mammal and/or interferes with one or more B cell functions, e.g. by reducing or preventing a humoral response elicited by the B cell. The antagonist preferably is able to deplete B cells (i.e. reduce circulating B cell levels) in a mammal treated therewith. Such depletion may be achieved via various mechanisms such antibody-dependent cell mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native sequence peptides and small molecule antagonists which bind to the B cell marker, optionally conjugated with or fused to a cytotoxic agent. The preferred antagonist comprises an antibody, more preferably a B cell depleting antibody.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457–92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652–656 (1998).

"Human effector cells" are leukocytes which express one or more FcRs and perform effector functions. Preferably, the cells express at least FcγRIII and carry out ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FCR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daeron, Annu. Rev. Immunol. 15:203–234 (1997)). FcRs are reviewed in Ravetch and Kinet, Annu. Rev. Immunol 9:457–92 (1991); Capel et al., Immunomethods 4:25–34 (1994); and de Haas et al., J. Lab. Clin. Med. 126:330–41 (1995). Other FcRs, including those to be identified in the future, are encompassed by the term "FCR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Complement dependent cytotoxicity" or "CDC" refer to the ability of a molecule to lyse a target in the presence of complement. The complement activation pathway is initiated by the binding of the first component of the complement system (Clq) to a molecule (e.g. an antibody) complexed with a cognate antigen. To assess complement activation, a CDC assay, e.g. as described in Gazzano-Santoro et al., J. Immunol. Methods 202:163 (1996), may be performed.

"Growth inhibitory" antagonists are those which prevent or reduce proliferation of a cell expressing an antigen to which the antagonist binds. For example, the antagonist may prevent or reduce proliferation of B cells in vitro and/or in vivo.

Antagonists which "induce apoptosis" are those which induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding or variable region thereof. Examples of antibody fragments include Fab, Fab', F(ab')2, and Fv fragments; diabodies; linear antibodies; single-chain antibody molecules; and multispecific antibodies formed from antibody fragments.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a P-sheet configuration, connected by three hypervariable regions, which form loops connecting, and in some cases forming part of, the (3 sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fob" fragments, each with a single antigen-binding site, and a residual "Fc" fragment, whose name reflects its ability to crystallize readily. Pepsin treatment yields an F(ab'2 fragment that has two antigen-binding sites and is still capable of crosslinking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')Z antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (x) and lambda (k), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called a, 8, s, y, and R, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore, eds., Springer-Verlag, New York, pp. 269–315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., *Proc. Natl. Acad. Sci. USA*, 90:6444–6448 (1993).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624–628 (1991) and Marks et al., *J. Mol. Biol.*, 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci.* USA, 81:6851–6855 (1984)). Chimeric antibodies of interest herein include "primatized" antibodies comprising variable domain antigen binding sequences derived from a non-human primate (e.g. Old World Monkey, such as baboon, rhesus or cynomolgus monkey) and human constant region sequences (U.S. Pat No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al., *Nature* 332:323–329 (1988); and Presta, *Curr. Op. Struct. Biol.* 2:593–596 (1992).

The term "hypervariable region" when used herein refers to the amino acid residues of an antibody which are responsible for antigen-binding. The hypervariable region comprises amino acid residues from a "complementarity determining region" or "CDR" (e.g. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk *J. Mol. Biol.* 196:901–917 (1987)). "Framework" or "FR" residues are those variable domain residues other than the hypervariable region residues as herein defined. An antagonist "which binds" an antigen of interest, e.g. a B cell surface marker, is one capable of binding that antigen with sufficient affinity and/or avidity such that the antagonist is useful as a therapeutic agent for targeting a cell expressing the antigen.

Examples of antibodies which bind the CD20 antigen include: "C2B8" which is now called "rituximab" ("RITUXAN®") (U.S. Pat. No. 5,736,137, expressly incorporated herein by reference); the yttrium-[90]-labeled 2138 murine antibody designated "Y2B8" (U.S. Pat. No. 5,736,137, expressly incorporated herein by reference); murine IgG2a "131" optionally labeled with 1311 to generate the "1311-B1" antibody (BEXXARTM®) (U.S. Pat. No. 5,595,721, expressly incorporated herein by reference); murine monoclonal antibody "1F5" (Press et al. *Blood* 69(2):584–591 (1987)); "chimeric 2H7" antibody (U.S. Pat. No. 5,677,180, expressly incorporated herein by reference); and rnonoclonal antibodies L27, G28-2, 93-1133, B-C1 or NU-B2 available from the International Leukocyte Typing Workshop (Valentine et al., In: *Leukocyte Typing III* (McMichael, Ed., p. 440, Oxford University Press (1987)). Examples of antibodies which bind the CD19 antigen include the anti-CD19 antibodies in Hekman et al., *Cancer Immunol. Immunother.* 32:364–372 (1991) and Vlasveld et al. Cancer Immunol. Immunother. 40:37–47(1995); and the B4 antibody in Kiesel et al. *Leukemia Research* 11, 12: 1119 (1987).

The terms "rituximab" or "RITUXAN®" herein refer to the genetically engineered chimeric murine/human mono clonal antibody directed against the CD20 antigen and designated "C2B8" in U.S. Pat. No. 5,736,137, expressly incorporated herein by reference. The antibody is an IgG, kappa immunoglobulin containing murine light and heavy chain variable region sequences and human constant region sequences. Rituximab has a binding affinity for the CD20 antigen of approximately 8.0 nM.

An "isolated" antagonist is one which has been identified and separated and/or recovered from a component of its natural environment. Contaminant components of its natural environment are materials which would interfere with diagnostic or therapeutic uses for the antagonist, and may include enzymes, hormones, and other pro teinaceous or nonproteinaceous solutes. In preferred embodiments, the antagonist will be purified (1) to greater than 95% by weight of antagonist as determined by the Lowry method, and most preferably more than 99% by weight, (2) to a degree sufficient to obtain at least 15 residues of N-terminal or internal amino acid sequence by use of a spinning cup sequenator, or (3) to homogeneity by SD S-PAGE under reducing or nonreducing conditions using Coomassie blue or, preferably, silver stain. Isolated antagonist includes the antagonist in situ within recombinant cells since at least one component of the antagonist's natural environment will not be present. Ordinarily, however, isolated antagonist will be prepared by at least one purification step. "Mammal" for purposes of treatment refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

The expression "therapeutically effective amount" refers to an amount of the antagonist which is effective for preventing, ameliorating or treating the autoimmune disease in question. The term "immunosuppressive agent" as used herein for adjunct therapy refers to substances that act to suppress or mask the immune system of the mammal being treated herein. This would include substances that suppress cytokine production, downregulate or suppress self-antigen expression, or mask the MHC antigens.

Examples of such agents include 2-amino-6-aryl-5-substituted pyrimidines (see U.S. Pat. No. 4,665,077, the disclosure of which is incorporated herein by reference); azathioprine; cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-y, -(3, or-a antibodies, anti-tumomecrosis factor-a antibodies, anti-tumomecrosis factor-(i antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably antiCD3 or anti-CD4/CD4a antibodies; soluble peptide containing a LFA-3 binding domain (WO 90/08187 published Jul. 26, 1990); streptokinase; TGF-0; streptodomase; RNA or DNA from the host; FK506; RS-61443; deoxyspergualin; rapamycin; T-cell receptor (Cohen et al., U.S. Pat. No. 5,114,721); T-cell receptor fragments (Offner et al., Science 251: 430–432 (1991); WO 90/11294; Ianeway, Nature, 341: 482 (1989); and WO 91/01133); and T cell receptor antibodies (EP 340,109) such as TLOB9.

The term "cytotoxic agent" as used herein refers to a substance that inhibits or prevents the function of cells and/or causes destruction of cells. The term is intended to include radioactive isotopes (e.g. $I^{113}$, $Y^{90}$, $Ar^{211}$, $P^{32}$, $Re^{188}$, $Rc^{186}$, $SM^{153}$, $B^{212}$ and others), chemotherapeutic agents, and toxins such as small molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXANTM®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembiehin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLO, Bristol-Myers Squibb Oncology, Princeton, N.J.) and doxetaxel (TAXOTEW, Rh6ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and -0; mullerian-inhibiting substance; mouse gonadotropin-associated peptide; inhibin; activin; vascular endothelial growth factor; integrin; thrombopoietin (TPO); nerve growth factors such as NGF-P; platelet growth factor; transforming growth factors (TGFS) such as TGF-a and TGF-0; insulin-like growth factor-I and -II; erythropoietin (EPO); osteoinductive factors; interferons such as interferon-a, -P, and -y; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-a or TNF-P; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wihnan, "Prodrugs in Cancer Chemotherapy" *Biochemical Society Transactions*, 14, pp. 375–382, 615th Meeting Belfast (1986) and Stella et al., "Prodrugs: A Chemical Approach to Targeted Drug Delivery," *Directed Drug Delivery*, Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, (3-lactam-containing prodrugs, optionally substituted phenoxyacetamide-containing prodrugs or optionally substituted phenylacetamide-containing prodrugs, 5 fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes. The term "package insert" is used to refer to instructions customarily included in commercial packages of therapeutic products, that contain information about the indications, usage, dosage, administration, contraindications and/or warnings concerning the use of such therapeutic products.

II. Production of Antagonists

The methods and articles of manufacture of the present invention use, or incorporate, an antagonist which binds to a B cell surface marker and/or a cytokine. Accordingly, methods for generating such antagonists will be described here. The B cell surface marker or cytokine to be used for production of, or screening for, antagonist(s) may be, e.g., a soluble form of the antigen or a portion thereof, containing the desired epitope. Alternatively, or additionally, cells expressing the B cell surface marker at their cell surface can be used to generate, or screen for, antagonist(s). Other forms of the B cell surface marker useful for generating antagonists will be apparent to those skilled in the art. Preferably, the B cell surface marker is the CD19 or CD20 antigen. Preferably, the cytokine is IL-10.

While the preferred antagonist is an antibody, antagonists other than antibodies are contemplated herein. For example, the antagonist may comprise a small molecule antagonist optionally fused to, or conjugated with, a cytotoxic agent (such as those described herein). Libraries of small molecules may be screened against the B cell surface marker of interest herein in order to identify a small molecule which binds to that antigen. The small molecule may further be screened for its antagonistic properties and/or conjugated with a cytotoxic agent.

The antagonist may also be a peptide generated by rational design or by phage display (see, e.g., WO98/35036 published Aug. 13, 1998). In one embodiment, the molecule of choice may be a "CDR mimic" or antibody analogue designed based on the CDRs of an antibody. While such peptides may be antagonistic by themselves, the peptide may optionally be fused to a cytotoxic agent so as to add or enhance antagonistic properties of the peptide.

A description follows as to exemplary techniques for the production of the antibody antagonists used in accordance with the present invention.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOC12, or RIN=C=NR, where R and RI are different alkyl groups. Animals are immunized against the antigen, immunogenic conjugates, or derivatives by combining, e.g., 100 pg or 5 wg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, Le., the individual antibodies comprising the population are identical except for possible naturally occurring mutations that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse human heteromyeloma cell lines also have been described for the production of human monoclonal antibodies [Kozbor, *J. Immunol.*, 133:3001 (1984); Brodeur et al., *Monoclonal Antibody Production Techniques and Applications*, pp. 51–63 (Marcel Dekker, Inc., New York, 1987)].

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affmity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Phickthun, Immunol. Revs., 130:151–188 (1992).

In a further embodiment, antibodies or antibody fragments can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *BiolTechnology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al, *Proc. Natl. Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al, *Nature*, 332:323–327 (1988); Verhoeyen et al., *Science*, 239:1534–1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al, *J. Immunol*, 151:2296 (1993); Chothia et al., *J. Mol. Biol*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993); and U.S. Pat. Nos. 5,591,669, 5,589,369 and 5,545,807. Alternatively, phage display technology (McCafferty et al., *Nature* 348:552–553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g. Johnson, Kevin S. and Chiswell, David J., *Current Opinion in Structural Biology* 3:564–571(1993). Several sources of V-gene segments can be used for phage display. Clackson et al., *Nature*, 352: 624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581–597 (1991), or Griffith et al., *EMBO J.* 12:725–734 (1993). See, also, U.S. Pat. Nos. 5,565,332 and 5,573,905. Human antibodies may also be generated by in vitro activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-Sli fragments can be directly recovered from *E. coli* and chemically coupled to form F(ab')2 fragments [Carter et al., Bio/Technology 10:163–167 (1992)]. According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-a, vinca alkaloid, ricin A chain, methotrexate or radioactive isotope hapten). Bispecific antibodies can be prepared as full length antibodies or antibody fragments (e.g. F(ab')Z bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J*, 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain.

Accordingly, the VH arid VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Antibodies with more than two valencies are contemplated. For example, trispecific antibodies can be prepared. Tutt et al. *J. Immunol.* 147: 60 (1991).

III. Conjugates and Other Modifications of the Antagonist

The antagonists used in the methods or included in the articles of manufacture herein are optionally conjugated to a cytotoxic agent. Chemotherapeutic agents useful in the generation of such antagonist-cytotoxic agent conjugates have been described above.

Conjugates of an antagonist and one or more small molecule toxins, such as a calicheamicin, a maytansine (U.S. Pat. No. 5,208,020), a trichothene, and CC1065 are also contemplated herein. In one embodiment of the invention, the antagonist is conjugated to one or more maytansine molecules (e.g. about 1 to about 10 maytansinemolecules per antagonist molecule). Maytansine may, for example, be converted to May-SS-Me which may be reduced to May-SH3 and reacted with modified antagonist (Chari et al. *Cancer Research* 52: 127–131 (1992)) to generate a maytansinoid-antagonist conjugate.

Alternatively, the antagonist is conjugated to one or more calicheamicin molecules. The calicheamicin family of antibiotics are capable of producing double-stranded DNA breaks at sub-picomolar concentrations. Structural analogues of calicheamicin which may be used include, but are not limited to, 'yJ1, a21, a31, N-acetyl-yl', PSAG and 011 (Hinman et al. *Cancer Research* 53: 3336–3342 (1993) and Lode et al. *Cancer Research* 58: 2925–2928 (1998)).

Enzymatically active toxins and fragments thereofwhich can be used include diphtheria A chain, nonbinding active fragments of diphtheria toxin, exotoxin A chain (from *Pseudomonas aeruginosa*), ricin A chain, abrin A chain, modeccin A chain, alpha-sarcin, 4leuritesfordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates antagonist conjugated with a compound with nucleolytic activity (e.g. a ribonuclease or a DNA endonuclease such as a deoxyribonuclease; DNase). A variety of radioactive isotopes are available for the production of radioconjugated antagonists. Examples include $At^{211}$, $I^{131}$, $I^{125}$, $Y^{90}$ Re 186, Re 188, Sm153, Bi212 P32 and radioactive isotopes of Lu. Conjugates of the antagonist and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aidehydes (such as glutareldehyde), bis azido compounds (such as bis (p-azidobenzoyl) hexanediamine), bis-diazonium derivatives (such as bis-(pdiazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antagonist. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127–131 (1992)) may be used. Alternatively, a fusion protein comprising the antagonist and cytotoxic agent may be made, e.g. by recombinant techniques or peptide synthesis.

In yet another embodiment, the antagonist may be conjugated to a "receptor" (such streptavidin) for utilization in tumor pretargeting wherein the antagonist-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). The antagonists of the present invention may also be conjugated with a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate cleaving enzymes such as li-galactosidase and neuraminidase useful for converting glycosylated prodrugs into free drugs; (3-lactamase useful for converting drugs derivatized with (3-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457–458 (1987)). Antagonist-abzyme conjugates can be prepared as described herein for delivery of the abzyme to a tumor cell population.

The enzymes of this invention can be covalently bound to the antagonist by techniques well known in the art such as the use of the heterobifunctional crosslinking reagents discussed above. Alternatively, fusion proteins comprising at least the antigen binding region of an antagonist of the invention linked to at least a functionally active portion of an enzyme of the invention can be constructed using recombinant DNA techniques well known in the art [see, e.g., Neuberger et al., *Nature*, 312: 604–608 (1984)].

Other modifications of the antagonist are contemplated herein. For example, the antagonist may be linked to one of a variety of nonproteinaceous polymers, e.g., polyethylene glycol, polypropylene glycol, polyoxyalkylenes, or copolymers of polyethylene glycol and polypropylene glycol. The antagonists disclosed herein may also be formulated as liposomes. Liposomes containing the antagonist are prepared by methods known in the art, such as described in Epstein et al., *Proc. Matl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al., *J. Biol. Chem.* 257: 286–288 (1982) via a disulfide interchange reaction. A chemotherapeutic agent is optionally contained within the liposome. See Gabizon et al. *J. National Cancer Inst.* 81(19)1484 (1989). Amino acid sequence modification(s) of protein or peptide antagonists described herein are contemplated. For example, it may be desirable to improve the binding affinity and/or other biological properties of the antagonist.

Amino acid sequence variants of the antagonist are prepared by introducing appropriate nucleotide changes into the antagonist nucleic acid, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics. The amino acid changes also may alter post-translational processes of the antagonist, such as changing the number or position of glycosylation sites.

A useful method for identification of certain residues or regions of the antagonist that are preferred locations for mutagenesis is called "alanine scanning mutagenesis" as described by Cunningham and Wells *Science*, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antagonist variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by different residue. The sites of greatest interest for substitutional mutagenesis of antibody antagonists include the hypervariable regions, but FR alterations are also contemplated.

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gin; asn | lys |
| Asn (N) | gin; his; asp, lys; arg | gln |
| Asp (D) | glu; asn | glu |
| Cys (C) | ser; ala | ser |
| Gin (Q) | asn; glu | asn |
| Glu (E) | asp; gin | asp |
| Gly (G) | ala | ala |
| His (H) | asn; gin; lys; arg | arg |
| Ile (I) | leu; val; met; ala; phe; norleucine | ICU |
| Lea (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| TIP (W) | tyr; phe | tyr |
| Tyr (Y) | trp; phe; thr; ser | phe |
| Val (V) | ile; leu; met; phe; ala; norleucine | ICU |

Substantial modifications in the biological properties of the antagonist are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the antagonist also may be substituted, generally with serine, to improve the oxidative stability of the molecule and prevent aberrant crosslinking. Conversely, cysteine bond(s) may be added to the antagonist to improve its stability (particularly where the antagonist is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6–7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antagonist alters the original glycosylation pattern of the antagonist. By altering is meant deleting one or more carbohydrate moieties found in the antagonist, and/or adding one or more glycosylation sites that are not present in the antagonist.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antagonist is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antagonist (for O-linked glycosylation sites).

Nucleic acid molecules encoding amino acid sequence variants of the antagonist are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the antagonist.

It may be desirable to modify the antagonist of the invention with respect to effector function, e.g. so as to enhance antigen-dependent cell-mediated cyotoxicity (ADCC) and/or complement dependent cytotoxicity (CDC) of the antagonist. This may be achieved by introducing one or more amino acid substitutions in an Fc region of an antibody antagonist. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp. Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al. *Cancer Research* 53:2560–2565 (1993). Alternatively, an antibody can be engineered which has dual Fc regions and may thereby have enhanced complement lysis and ADCC capabilities. See Stevenson et al. *Anti-Cancer Drug Design* 3:219–230 (1989).

To increase the serum half life of the antagonist, one may incorporate a salvage receptor binding epitope into the antagonist (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

IV. Pharmaceutical Formulations

Therapeutic formulations of the antagonists used in accordance with the present invention are prepared for storage by mixing an antagonist or antagonists having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418, expressly incorporated herein by reference. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2–8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound zi.; necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antagonist present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly (methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations maybe prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Treatment with the Antagonist

A composition comprising an antagonist which binds to a B cell surface antigen and a composition which contains a cytokine antagonist, e.g. an antibody, wherein both may be in the same composition will be formulated, dosed, and administered in a fashion consistent with good medical practice. Preferably, the anti-cytokine will comprise an anti-IL10 antibody and the B cell antagonist will comprise a B cell depleting antibody, preferably an anti-CD20 antibody such as RITUXAN® (rituximab). Factors for consideration in this context include the particular disease or disorder being treated, the particular mammal being treated, the clinical condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

As a general proposition, the therapeutically effective amount of the antagonist administered parenterally per dose will be in the range of about 0.1 to 20 mg/kg of patient body weight per day, with the typical initial range of antagonist used being in the range of about 2 to 10 mg/kg.

The preferred antagonist is an antibody, e.g. an antibody such as RITUXAN®, (rituximab), which is not conjugated to a cytotoxic agent. Suitable dosages for an unconjugated antibody are, for example, in the range from about 20 mg/m2 to about 1000 mg/m2. In one embodiment, the dosage of the antibody differs from that presently recommended for RITUXAN® (rituximab). For example, one may administer to the patient one or more doses of substantially less than 375 mg/m2 of the antibody, e.g. where the dose is in the range from about 20 mg/mz to about 250 mg/m2, for example from about 50 mg/m2 to about 200 mg/m2.

Moreover, one may administer one or more initial dose(s) of the antibody followed by one or more subsequent dose(s), wherein the mg/m2 dose of the antibody in the subsequent dose(s) exceeds the mg/m2 dose of the antibody in the initial dose(s). For example, the initial dose may be in the range from about 20 mg/m2 to about 250 mg/m2 (e.g. from about 50 mg/m2 to about 200 mg/mz) and the subsequent dose may be in the range from about 250 mg/m2 to about 1000 mg/m2.

As noted above, however, these suggested amounts of antagonist are subject to a great deal of therapeutic discretion. The key factor in selecting an appropriate dose and scheduling is the result obtained, as indicated above.

For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

The antagonist is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration.

In addition, the antagonist may suitably be administered by pulse infusion, e.g., with declining doses of the antagonist. Preferably the dosing is given by injections, most preferably intravenous or subcutaneous injections, depending in part on whether the administration is brief or chronic.

One may administer other compounds, such as cytotoxic agents, chemotherapeutic agents, immunosuppressive agents and/or cytokines with the antagonists herein. The combined administration includes coadministration, using separate formulations or a single pharmaceutical formulation, and consecutive administration in either order, wherein preferably there is a time period while both (or all) active agents simultaneously exert their biological activities.

Aside from administration of protein antagonists to the patient the present application contemplates administration of antagonists by gene therapy. Such administration of nucleic acid encoding the antagonist is encompassed by the expression "administering a therapeutically effective amount of an antagonist". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429–4432 (1987); and Wagner et al., *Proc. Natl. Acad. Sci.* USA 87:3410–3414 (1990). For review of the currently known gene marking and gene therapy protocols see Anderson et al., *Science* 256:808–813 (1992). See also WO 93/25673 and the references cited therein.

VI. Articles of Manufacture

In another embodiment of the invention, an article of manufacture containing materials useful for the treatment of the diseases or disorders described above is provided. The article of manufacture comprises a container and a label or package insert on or associated with the container. Suitable containers include, for example, bottles, vials, syringes, etc. The containers maybe formed from a variety of materials such as glass or plastic. The container holds or contains a composition which is effective for treating the disease or disorder of choice and may have a sterile access port (for example the container may be an intravenous solution bag or a vial having a stopper pierceable by a hypodermic injection needle). At least one active agent in the composition is the antagonist which binds a B cell surface marker. Preferably CD20, and an anti-cytokine antibody, e.g. an anti-IL10 antibody. The label or package insert indicates that the composition is used for treating a patient having or predisposed to an autoimmune disease, such as those listed herein. The article of manufacture may further comprise a second container comprising a pharmaceutically-acceptable diluent buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting Examples. The disclosure of all citations in the specification are expressly incorporated by reference.

EXAMPLES

Example 1

Treatment of Non-Hodgkin's Lymphoma

A patient with non-Hodgkin's lymphoma is intravenously administered an anti-IL10 antibody at a dosage of 50 mg/m$^2$ IV weekly for four weeks. Thereafter, the patient is administered RITUXAN® (rituximab) intravenously according to the following dosage schedules:

(A) 50 mg/m$^2$ IV day 1
150 mg/m$^2$ IV days on 8, 15 & 22
(B) 150 mg/m$^2$ IV day 1
375 mg/m$^2$ IV on days 8, 15 & 22
(C) 375 mg/m$^2$ IV on days 1, 8, 15 & 22

This same patient is administered CHOP chemotherapy according to the regimen described in U.S. Pat. No. 5,736,137.

After treatment, the patient is monitored to evaluate the effect on lymphoma status, e.g., number and size of tumors.

Example 2

Treatment of Solid Tumor in Advanced Stage

A patient having an advanced colorectal cancer characterized by B cell involvement is treated concurrently with an anti-IL10 antibody and RITUXAN® (rituximab) at the same dosages as in Example 1.

After treatment the patient is evaluated to determine whether such treatment has resulted in an anti-tumor response, e.g., based on tumor shrinkage, lower tumor antigen expression or other means of evaluating disease prognosis.

What is claimed:

1. A method of treating B cell lymphoma in a patient in need of such treatment which method includes the administration of anti-IL10 antibody and at least one B cell depleting antibody.

2. The method of claim 1 wherein said B cell depleting antibody binds to a B cell antigen from the group consisting of CD19, CD20, CD22, CD23, CD27, CD37, CD53, CD72, CD73, CD74, CDω78, CD79a, CD79b, CD80, CD81, CD82, CD83, CDw84, CD85 and CD86.

3. A method of treating B cell lymphoma in a patient in need of such treatment which method comprises the administration of an anti-IL10 antibody and a B cell depleting anti-CD20 or anti-CD22 antibody.

4. A method of treating B cell lymphoma in a patient in need of such treatment comprising the administration of an anti-IL10 antibody and a B cell depleting anti-CD20 antibody.

5. A method of treating non-Hodgkin's lymphoma in a patient in need of such treatment comprising the administration of an anti-IL10 antibody and a B cell depleting antibody.

6. A method of treating non-Hodgkin's lymphoma in a patient in need of such treatment comprising the administration of an anti-IL10 antibody and a B cell depleting anti-CD20 antibody.

7. A method of treating non-Hodgkin's lymphoma in a patient in need of such treatment comprising the administration of an anti-IL10 antibody and a B cell depleting anti-CD22 antibody.

8. The method of claim 4 wherein said antibody is rituximab (ATCC No. HB-69119).

9. The method of claim 6 wherein said antibody is rituximab (ATCC No. HB-69119).

10. A combination therapy for treating B cell lymphoma in a patient comprising the administration of a therapeutically effective amount of an anti-IL10 antibody, a B cell depleting anti-CD20 antibody and chemotherapy.

11. The method of claim 10 wherein said anti CD20 antibody is rituximab (ATTC No. HB-69119).

12. The method of claim 10 wherein said patient has relapsed following previous treatment with a B cell depleting antibody.

13. The method of claim 12 wherein said antibody is rituximab (ATTC No. HB-69119).

14. The method of claim 2 wherein the B cell depleting antibody binds CD20.

15. The method of claim 2 wherein the B cell depleting antibody binds CD23.

16. The method of claim 14 wherein said antibody is a chimeric anti-CD20 antibody.

17. The method of claim 16 wherein said chimeric anti-CD20 antibody is rituximab (ATCC No. HB-69119).

18. The method of claim 1 wherein said treating is combined with chemotherapy.

19. The method of claim 1 wherein said B cell lymphoma is selected from the group consisting of low grade/follicular non-Hodgkin's lymphoma (NHL), small lymphocytic (SL) NHL, intennediate grade/follicular NHL, intermediate grade diffuse NHL, high grade immunoblastic NHL, high grade lymphoblastic NHL, high grade immunoblastic NHL, high grade lymphoblastic NHL, high grade small non-cleaved cell NHL, bulky disease NHL and Waldenstrom's Macroglobulinemia.

20. The method of claim 1 wherein said antibodies are administered by intravenous, intramuscular, intratumoeral or intraperitoneal administration.

21. The method of claim 18 wherein said chemotherapy is selected from the group consisting of CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA (with or without subsequent G-CSF treatment), VAD, M&P, C-Weekly, ABCM, MOPP, DHAP, daunorubicin, doxorubicin, methotrexate, and cisplatin.

22. The method of claim 1 wherein either or both of said antibodies are human, humanized or chimeric antibodies.

23. The method of claim 1 wherein the dosage of said antibodies range from 0.01 to 1000 mg/kg body weight.

24. A method of treating B cell lymphoma in a patient in need of such treatment comprising the administration of an anti-R10 antibody and a B cell depleting anti-CD20 antibody, wherein the anti-CD20 antibody comprises the heavy chain variable region of C2B8, and the light chain variable region of C2B8.

25. The method of claim 24, wherein the anti-CD20 antibody further comprises human constant regions.

26. The method of claim 6, wherein the anti-CD20 antibody comprises the heavy chain variable region of C2B8, and the light chain variable region of C2B8.

27. The method of claim 26, wherein the anti-CD20 antibody further comprises human constant regions.

28. The method of claim 10, wherein the anti-CD20 antibody comprises the heavy chain variable region of C2B8, and the light chain variable region of C2B8.

29. The method of claim 28, wherein the anti-CD20 antibody further comprises human constant regions.

* * * * *

UNITED STATES PATENT AND TRADEMARK OFFICE
CERTIFICATE OF CORRECTION

PATENT NO. : 6,896,885 B2
DATED : May 24, 2005
INVENTOR(S) : Nabil Hanna

It is certified that error appears in the above-identified patent and that said Letters Patent is hereby corrected as shown below:

Column 36,
Lines 13 and 15, replace "said antibody" with -- said anti-CD20 antibody --.
Lines 21-22, replace "said anti CD20" and "ATTC" with -- said anti-CD20 -- and -- ATCC --, respectively.
Lines 26-27, replace "said antibody" and "ATTC" with -- said anti-CD20 antibody -- and -- ATCC --, respectively.
Line 64, replace "anti-R10" with -- anti-IL10 --.

Signed and Sealed this

Sixth Day of September, 2005

JON W. DUDAS
*Director of the United States Patent and Trademark Office*